(12) United States Patent
Ridder et al.

(10) Patent No.: US 8,815,520 B2
(45) Date of Patent: *Aug. 26, 2014

(54) METHOD FOR DISCRIMINATION OF METAPLASIAS FROM NEOPLASTIC OR PRENEOPLASTIC LESIONS

(75) Inventors: Ruediger Ridder, Schriesheim (DE); Magnus Von Knebel Doeberitz, Heidelberg (DE); Peter Martin, Gaiberg (DE)

(73) Assignee: Ventana Medical Systems, Inc., Tucson, AZ (US)

( * ) Notice: Subject to any disclaimer, the term of this patent is extended or adjusted under 35 U.S.C. 154(b) by 359 days.

This patent is subject to a terminal disclaimer.

(21) Appl. No.: 13/137,547

(22) Filed: Aug. 25, 2011

(65) Prior Publication Data

US 2012/0052510 A1   Mar. 1, 2012

Related U.S. Application Data

(63) Continuation of application No. 12/164,934, filed on Jun. 30, 2008, now Pat. No. 8,043,819, which is a continuation of application No. 10/511,108, filed as application No. PCT/EP03/50096 on Apr. 8, 2003, now Pat. No. 7,422,859.

(30) Foreign Application Priority Data

Apr. 9, 2002   (EP) .................................... 02007954

(51) Int. Cl.
*G01N 33/53*   (2006.01)
*C12Q 1/68*   (2006.01)
*G01N 33/574*   (2006.01)

(52) U.S. Cl.
CPC .... *G01N 33/57411* (2013.01); *G01N 2333/025* (2013.01); *C12Q 1/6886* (2013.01)
USPC .......................................................... 435/7.1

(58) Field of Classification Search
CPC ...................................................... A61K 39/00
See application file for complete search history.

(56) References Cited

PUBLICATIONS

Tockman et al (Cancer Res., 1992, 52:2711s-2718s).*
Khan et al, Journal of Virology, Jun. 1993, 67(6): 3396-3403).*
Solomon et al. (2001, J. of the National Cancer Institute 93(4):293-299).*
Klaes et al. (2001, Int. J. Cancer 92:276-284).*
Guccione (Virology 293:20-25 (2002).*
Khan et al (Journal of Virology, Jun. 1993, 67(6): 3396-3403).*
von Knebel Doeberitz (2001, Dis. Markers 17(3):123-8 (abstract only).*
Patel et al (J Gen Virol, 1989, 70(Pt 1): 69-77).*

* cited by examiner

*Primary Examiner* — Sean Aeder
(74) *Attorney, Agent, or Firm* — Perkins Coie LLP; Viola T. Kung (57) ABSTRACT

The present invention relates to a method for discrimination of $p16^{INK4a}$ overexpressing metaplasias from neoplastic or preneoplastic $p16^{INK4a}$ overexpressing lesions by determination of the level of high risk HPV encoded gene-products such as e.g. HPV E2 and/or HPV E7 molecules in biological samples in the course of cytological testing procedures. The method thus enables for reduction of false positive results in the $p16^{INK4a}$ based detection of anogenital lesions in cytological testing procedures.

11 Claims, 6 Drawing Sheets
(6 of 6 Drawing Sheet(s) Filed in Color)

METHOD FOR DISCRIMINATION OF METAPLASIAS FROM NEOPLASTIC OR PRENEOPLASTIC LESIONS

This application is a continuation of U.S. patent application Ser. No. 12/164,934, filed Jun. 30, 2008 now U.S. Pat. No. 8,043,819, which is a continuation of U.S. patent application Ser. No. 10/511,108, filed Oct. 8, 2004, now U.S. Pat. No. 7,422,859, which is a national stage entry of Application No. PCT/EP2003/050096, filed Apr. 8, 2003, and claims priority to European Application No. 02007954.7, filed Apr. 9, 2002, which is incorporated by reference herein in its entirety, as if set forth fully herein.

The present invention relates to a method for discrimination of $p16^{INK4a}$ overexpressing metaplasias from neoplastic or preneoplastic $p16^{INK4a}$ overexpressing lesions by determination of the level of high risk HPV encoded gene-products such as e.g. HPV E2 or E7 molecules in biological samples in the course of cytological testing procedures. The method thus enables for reduction of false positive results in the $p16^{INK4a}$ based detection of anogenital lesions in cytological testing procedures.

The detection of the overexpression of $p16^{INK4a}$ in biological samples has proven as a useful marker in the detection of anogenital lesions such as carcinoma of the uterine cervix (see WO00/01845; Klaes et al., Int. J. Cancer: 92, 276-284 (2001)). The method based on $p16^{INK4a}$-specific immunochemical staining allows for a sensitive and specific identification of dysplastic cells in tissue section and in cytological samples.

In immuno-histochemical examinations of tissues neoplastic cells can be stained using a $p16^{INK4a}$ specific antibody mediated staining procedure. The histological diagnosis of neoplastic lesions can thus be supported by a staining based on a molecular marker characteristic for transformation of cells in anogenital lesions. The diagnosis, whether or not cells are neoplastic, in these procedures is not solely based on the $p16^{INK4a}$ specific staining, but does also rely on the histological information.

This is due to the fact, that in about 30% of samples metaplastic cells show some immunoreactivity with $p16^{INK4a}$ specific antibodies, and thus are stained in the course of the procedures. Yet the staining pattern yielded from these metaplastic cells differs from the pattern rendered from neoplastic lesions. Metaplastic cells give rise to a patchy or focal staining pattern, whereas neoplastic lesions give rise to diffuse staining patter. Moreover the staining intensities of metaplastic cells are predominantly less than that of neoplastic cells.

The common methods used in screening tests for the early detection of neoplasias do not employ histology based tests, but rather rely on cytological testing procedures. Yet especially in cases, when there is no histological information available concerning the architecture of tissues, such as for example in cytological examinations, testing for $p16^{INK4a}$ overexpression alone may lead to false positive results. This is due to the fact, that the metaplastic cells expressing $p16^{INK4a}$ at detectably elevated levels, may not be differentiated by means of a histological staining patterns.

The percentage of cells showing overexpression of $p16^{INK4a}$ increases in the course of emergence of dysplasias. So in neoplastic or preneoplastic stages, when only a restricted population of neoplastic or preneoplastic cells is present in samples the immunoreactivity of $p16^{INK4a}$ may be weak. This weak immunoreactivity may be of about the level as the level caused by metaplastic cells. In later stages of dysplasias the overall immunoreactivity of $p16^{INK4a}$ is stronger and so neoplastic lesions are easily discernible from metaplasias even in a cytological testing format. This might lead to cases, where the presence of metaplastic cells expressing $p16^{INK4a}$ might be confused with the presence of neoplastic cells, and thus producing a false positive result.

Especially in screening tests, where the detection of early stages of neoplasias is desirable this condition is quite unpleasant. This is especially true, as the $p16^{INK4a}$ based diagnosis has proven to be a valuable tool in histological examinations and the application in cytological based screening procedures would be able to enhance these established procedures.

To reduce false positive results in cytological testing formats and so to further enhance the fidelity of the $p16^{INK4a}$ mediated diagnosis of anogenital lesions a method for discriminating the metaplasias from neoplastic and dysplastic lesions would be desirable. The problem in the art especially pertains to early stages of neoplasias, when the percentage of cells showing $p16^{INK4a}$ overexpression is still at a level, that might be confused with levels of normally occurring $p16^{INK4a}$ overexpressing proliferating metaplastic cells. Thus useful means for solving the present problem have to involve parameters that characterize early stages of neoplasias of the anogenital tract. Any characteristics of dysplasias and/or neoplasias emerging during the progress of tumorigenesis, thus proving as diagnostic tools for high grade dysplasias, and are limited in early stages of tumorigenesis are not suitable for the method according to the present invention.

A method for the discrimination of metaplasias from neoplastic and preneoplastic lesions is provided within the embodiments claimed according to the present invention.

For supporting the discrimination of metaplasias from neoplastic lesions in testing procedures based on the overexpression of $p16^{INK4a}$ a marker molecule would be desirable, that is expressed in neoplastic and/or preneoplastic cells and tissues and, which is not expressed in metaplastic cells.

E2 of HPV is especially expressed in lower grade CIN lesions and the expression decreases with ascending CIN grades (Stevenson et al., J. Gen. Virol., 81, 1825-32 (2000)). In most invasive carcinomas no expression of E2 protein is detectable. This may be due to the fact, that parts of the E2 gene are lost during integration of the HPV DNA into the host genome. Thus in persistent HPV infections having integrated HPV DNA no or low E2 expression may be detected.

Due to these facts E2 protein proves to be a marker for early stages of lesions associated with high risk HPV infections. In contrast $p16^{INK4a}$ is a marker which is overexpressed even in early stages of anogenital lesions, the expression level of which increases in the course of progression of dysplastic lesions. The fact that E2 is especially expressed in early stages of neoplasias makes it particularly useful for early detection methods. The high expression level of E2 protein in early stages of HPV infection allows to identify infected cells, before there is an abundant number of copies of the virus present in the tested cells.

The L1 and L2 gene-products are also useful for the method according to the present invention due to their high expression level predominantly in early stages of viral infection before integration has occurred. The expression of these gene-products is also reduced in persistent infection of HPV.

The inventors now have found, that cells expressing high risk HPV gene-products such as HPV E2 may serve to discriminate early neoplastic or dysplastic lesions detectable by $p16^{INK4a}$ specific immuno-chemical staining from metaplasias, which may also comprise cells immunoreactive with $p16^{INK4a}$, in the course of cytological testing procedures.

Cells expressing other HPV encoded gene-products, that are detectable on an expression level as mRNA or polypeptide in neoplastic stages or preneoplastic stages, may also serve for the discrimination of neoplastic and/or preneoplastic lesions from metaplasias overexpressing p16$^{INK4a}$ according to the present invention. Examples of such HPV encoded gene-products include HPV E6, E7, L1 or L2 proteins or mRNA.

The present invention relates to a method for discrimination of neoplastic, preneoplastic and/or dysplastic lesions from metaplasias comprising p16$^{INK4a}$ overexpressing cells, in biological samples in a cytological testing procedure based on the detection of the presence or absence of cells expressing high risk HPV gene-products in said biological samples. HPV gene-products useful for the method disclosed herein are gene-products, which are highly expressed especially in early stages of neoplastic and preneoplastic lesions. In one embodiment of the invention HPV E2 protein or mRNA may serve as a marker for discrimination of metaplasias from early neoplastic or preneoplastic lesions in samples. Furthermore HPV E6, E7, L1 or L2 protein and/or mRNA also proved to be suitable for performing the discrimination according to the invention disclosed herein.

Discrimination as used in the context of the present invention shall comprise an assessment whether a sample is to be classified in one or another way. In a preferred embodiment of the invention the discrimination pertains to the assessment of a tissue or components thereof being neoplastic or being metaplastic. Thus the discrimination as used herein is a judgement about the growth properties of cells in a sample.

The discrimination according to the present invention is based on the presence or absence of cells expressing a high risk HPV gene-product and on the presence or absence of cells overexpressing p16$^{INK4a}$ in said sample. The cells expressing the high risk HPV gene-products such as E2 need not be the same cells as those overexpressing p16INK4a although the expression of both marker molecules may occur in the same cells.

Thus the presence of cells expressing E2 gene-products in a sample simultaneously with the presence of cells overexpressing p16$^{INK4a}$ (other cells or the same cells coexpressing both markers) according to the present invention serves to discriminate neoplastic or preneoplastic lesions from metaplasias.

HPV encoded gene-products as used in the context of the present invention shall be any mRNA transcribed from a gene of the HPV genome or any polypeptide translated from such an mRNA. HPV gene-products suitable for the method according to the present invention are gene-products encoded by the E6, E7, L1 and L2 genes. In one especially preferred embodiment of the present invention the HPV geneproduct is encoded by the HPV E2 gene.

HPV herein means human papilloma virus. HPV as used herein shall comprise any high risk subtype of HPV. In a preferred embodiment of the present invention the HPV subtype is a cancer associated HPV subtype such as e.g. HPV 16, 18, 31, 33, 35, 39, 45, 51, 52, 56 and 58. In an especially preferred embodiment the HPV high risk subtypes are HPV 16, 18, 39 or HPV 45. Subtyping of the HPV shall comprise any method suitable of the determination of the particular HPV subtype present in a biological sample.

The method for detection of the level of the HPV encoded gene-products according to the present invention is any method, which is suited to detect very small amounts of specific biological molecules in biological samples. The detection reaction according to the present invention is a detection either on the level of nucleic acids or on the level of polypeptides.

The HPV gene-products may be detected using reagents that specifically recognise these molecules. The detection reaction for the HPV gene-products may comprise one or more reactions with detecting agents either recognizing the initial marker molecules or recognizing the prior molecules used to recognize other molecules.

The detection reaction further may comprise a reporter reaction indicating the presence or absence and/or the level of the HPV gene-products. The reporter reaction may be for example a reaction producing a coloured compound, a bioluminescence reaction, a fluorescence reaction, generally a radiation emitting reaction etc.

In a preferred embodiment, different marker molecules may be recognized by agents that produce different reporter signals, so that the signals referring to marker molecules could be distinguished. In one preferred embodiment of the invention the detection of the expression of high risk HPV gene-products is carried out simultaneously with the detection of the overexpression of p16$^{INK4a}$. In this case the reporter reaction may for example employ different fluorescent labels for the different molecules detected.

Applicable formats for the detection reaction according to the present invention may be, blotting techniques, such as Western-Blot, Southern-blot, Northern-blot. The blotting techniques are known to those of ordinary skill in the art and may be performed for example as electro-blots, semidry-blots, vacuum-blots or dot-blots. Amplification reaction may also be applicable for the detection of e.g. nucleic acid molecules.

In one preferred embodiment of the invention the detection of the level of HPV gene-products is carried out by detection of the respective mRNA or fragments thereof present in the sample. The means for detection of nucleic acid molecules are known to those skilled in the art. The procedure for the detection of nucleic acids can for example be carried out by a binding reaction of the molecule to be detected to complementary nucleic acid probes, proteins with binding specificity for the nucleic acids or any other entities specifically recognizing and binding to said nucleic acids.

This method can be performed as well in vitro as directly in situ for example in the course of a detecting staining reaction. Another way of detecting the HPV mRNAs in a sample performed in the method according to the present invention is an amplification reaction of nucleic acids, which can be carried out in a quantitative manner such as for example the polymerase chain reaction. In a preferred embodiment of the present invention real time RT PCR may be used to quantify the level of HPV mRNA in samples of tumors.

In another preferred embodiment of the invention the detection of the level of HPV gene-products is carried out by determining the level of expression of a protein. The determination of the HPV geneproduct on the protein level can for example be carried out in a reaction comprising a binding agent specific for the detection of the particular HPV polypeptide.

The binding agents can be used in many different detection techniques for example in western-blot, ELISA or immunoprecipitation. Generally polypeptide binding agent based detection can be carried out as well in vitro as directly in situ for example in the course of an immuno-histochemical staining reaction. Any other method for determining the amount of particular polypeptides in biological samples can be used according to the present invention.

Binding agents as used in the context of the present invention for the detection of the level of either HPV polypeptides or p16$^{INK4a}$ polypeptides may comprise antibodies and antigen-binding fragments, bifunctional hybrid antibodies, peptidomimetics containing minimal antigen-binding epitopes etc.

An antibody or antigen-binding agent is said to react specifically, if it reacts at a detectable level with a protein disclosed herein, and does not significantly react with other proteins. The antibodies according to the present invention may be monoclonal or polyclonal antibodies. As used herein, the term antibody or monoclonal antibody is meant to include intact molecules as well as antibody fragments. Moreover, antibodies of the present invention include chimeric, single chain, and humanized antibodies.

According to the present invention binding agents may be used isolated or in combination. By means of combination it is possible to achieve a higher degree of sensitivity. The term antibody, preferably, relates to antibodies which consist essentially of pooled monoclonal antibodies with different epitopic specificities, as well as distinct monoclonal antibody preparations.

Monoclonal antibodies are made from antigen containing fragments of the polypeptide of the invention using any of a variety of techniques known to those of ordinary skill in the art; see, e.g., Harlow and Lane, Antibodies: A Laboratory Manual, Cold Spring Harbor Laboratory, 1988. In one such technique, an immunogen comprising the antigenic polypeptide or a synthetic part thereof is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

The methods used for the detection of the presence or absence of overexpression of $p16^{INK4a}$ according to the present invention are the same methods mentioned above for the detection of HPV gene-products.

The HPV gene-products may according to the present invention be detected simultaneously with the presence or absence of the overexpression of $p16^{INK4a}$. In this context simultaneously according to the present invention shall mean either literally at the same instant or within the same testing procedure, whereby the single detection steps are temporally consecutive.

A sample according to the method of the present invention may comprise any sample comprising cells of anogenital origin. Samples may comprise e.g. secretions, smears, body fluids, and cell-samples.

In one embodiment of the present invention samples comprise cells of the uterine cervix. In a preferred embodiment of the present invention the sample of cervical cells may be prepared according to a classical Pap smear. In a further preferred embodiment of the present invention the sample may be prepared as a monolayer or thin layer preparation of the cytological specimen.

Preparation of a sample may comprise e.g. obtaining a sample of a tissue, of a body fluid, of cells from a patient. According to the present invention preparation of the sample may also comprise several steps of further preparations of the sample, such as preparation of dissections, spreading or applying the cells to be examined onto microscopic slides, preparation of tissue arrays, isolation of polypeptides or nucleic acids, preparation of solid phase fixed peptides or nucleic acids or preparation of beads, membranes or slides to which the molecules to be determined are coupled covalently or non-covalently.

The neoplastic lesions to which the method according to the present invention may be applied comprise any anogenital lesion, which is characterized by the overexpression of $p16^{INK4a}$, which furthermore shows expression of HPV gene-products. In one preferred embodiment of the present invention the anogenital lesion is a lesion of the uterine cervix.

Another aspect of the present invention is a testing kit for performing the method according to the present invention. The kit may be for example a diagnostic kit or a research kit.

A kit according to the present invention comprises at least an agent suitable for detecting the HPV gene-products and an agent suitable for the detection of the presence or absence of the overexpression of $p16^{INK4a}$.

Thus a kit according to present invention may comprise:
a) reagents for the detection of the HPV gene-products
b) reagents for the detection of the $p16^{INK4a}$ overexpression
c) reagents and buffers commonly used for carrying out the detection reaction, such as buffers, detection-markers, carrier substances and others
d) a $p16^{INK4a}$ sample for carrying out a positive control reaction
e) a HPV gene-product sample for carrying out a positive control reaction The reagents for the detection of the HPV gene-products and/or $p16^{INK4a}$ may include any agent capable of binding to the HPV gene-products and/or $p16^{INK4a}$ molecule. Such reagents may include proteins, polypeptides, nucleic acids, peptide nucleic acids, glycoproteins, proteoglycans, polysaccharide or lipids.

The HPV gene-product and/or $p16^{INK4a}$ sample for carrying out a positive control may comprise for example nucleic acids in applicable form, such as solution or salt, peptides in applicable form, tissue section samples or positive cells.

In a preferred embodiment of the invention the detection of the HPV gene-products and/or $p16^{INK4a}$ is carried out on the level of polypeptides. In this embodiment the binding agents may be for example antibodies specific for the HPV gene-products or $p16^{INK4a}$ or fragments thereof.

In another embodiment of the test kit the detection of the HPV gene-products and/or $p16^{INK4a}$ is carried out on the nucleic acid level. In this embodiment of the invention the reagent for the detection may be for example a nucleic acid probe or a primer reverse-complementary to said HPV gene product and/or $p16^{INK4a}$ nucleic acids.

The present invention provides a method for the discrimination of neoplastic and preneoplastic anogenital lesion identifiable by assessment of the overexpression of $p16^{INK4a}$ from metaplastic cells, which detectably express $p16^{INK4a}$ in the course of cytological testing procedures. The method is based on the detection of expressed gene-products of high risk HPV. It turned out, that high risk HPV gene-products expressed in high levels in the early stages of neoplasias and in preneoplasias are suitable for this discrimination. This is due to the fact, that the percentage of cells in a biological sample in early stages of neoplasias overexpressing $p16^{INK4a}$ renders a level of $p16^{INK4a}$ molecules, that there remains the possibility, that the level recurs to metaplastic rather than neoplastic cells. Thus the problem to be solved was to provide a method for discrimination between neoplastic and metaplastic cells especially in early stages of neoplasias, when cytological diagnostic methods based on the p16$^{INK4a}$ overexpression needs a further information for the identification of metaplastic cells.

Furthermore the present invention provides a kit for performing the method according to the present invention.

Figure 1:
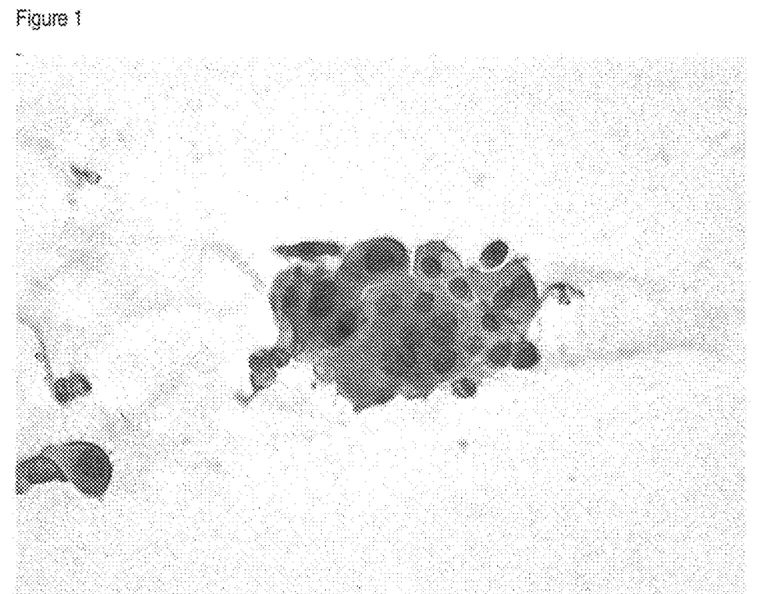
FIG. 1 Metaplastic cells immunochemically stained with an antibody specific for p16$^{INK4a}$; for experimental details see Example 1; the cells clearly react with the antibodies against p16$^{INK4a}$ FIG. 2 Metaplastic cells immunochemically stained with an antibody specific for HPV E2; for experimental details see Example 1; the cells do not show immunoreactivity with the polyclonal antibodies directed against HPV E2 protein FIG. 3 Metaplastic cells immunochemically stained with an antibody specific for HPV L1; for experimental details see Example 1; the cells do not show immunoreactivity with the polyclonal antibodies directed against HPV L1 protein FIG. 4 Dysplastic cells immunochemically stained with an antibody specific for p16$^{INK4a}$; for experimental details see Example 1; the cells clearly react with the antibodies against p16$^{INK4a}$ FIG. 5 Dysplastic cells immunochemically stained with an antibody specific for HPV E2; for experimental details see Example 1; the cells show clear immunoreactivity with the polyclonal antibodies directed against HPV E2 protein FIG. 6 Dysplastic cells immunochemically stained with an antibody specific for HPV L1; for experimental details see Example 1; the cells show clear immunoreactivity with the polyclonal antibodies directed against HPV L1 protein FIG. 7 Metaplastic cells immunochemically stained with an antibody specific for p16$^{INK4a}$; for experimental details see Example 3; the cells clearly react with the antibodies against p16$^{INK4a}$ FIG. 8 Metaplastic cells immunochemically stained with an antibody specific for HPV E7; for experimental details see Example 3; the cells do not show immunoreactivity with the monoclonal antibodies directed against HPV E7 protein FIG. 9 Dysplastic cells immunochemically stained with an antibody specific for p16$^{INK4a}$; for experimental details see Example 3; the cells clearly react with the antibodies against p16$^{INK4a}$ FIG. 10 Dysplastic cells immunochemically stained with an antibody specific for HPV E7; for experimental details see Example 3; the cells clearly react with the antibodies against HPV E7 protein FIG. 11 Dysplastic cells immunochemically doublestained with antibodies specific for HPV E7 and antibodies specific for p16$^{INK4a}$; for experimental details see Example 3; the cells clearly react with the antibodies against both HPV E7 and p16$^{INK4a}$ proteins.
Figure 2:
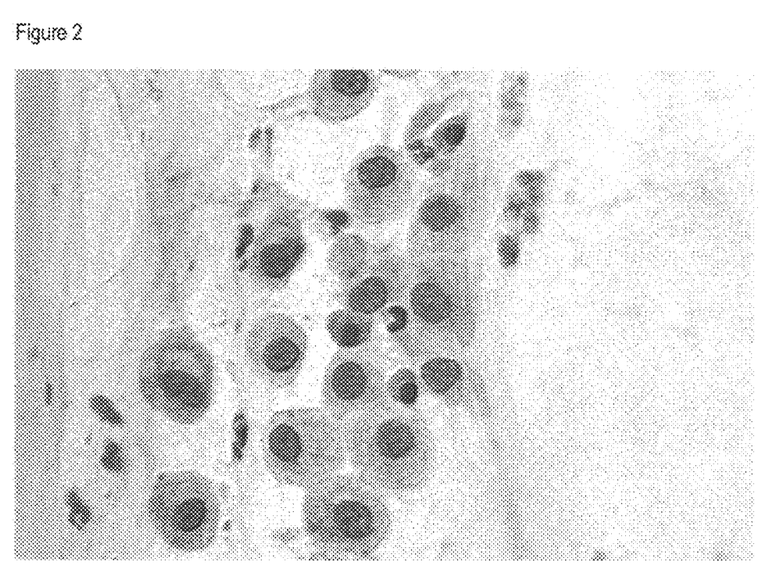
Figure 3:
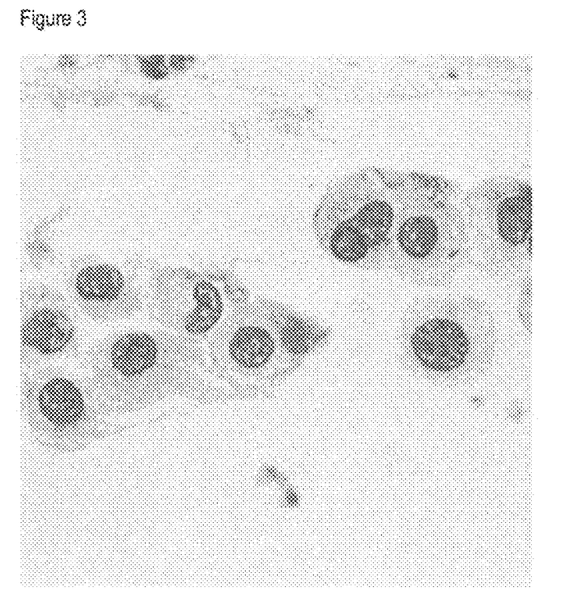
Figure 4:
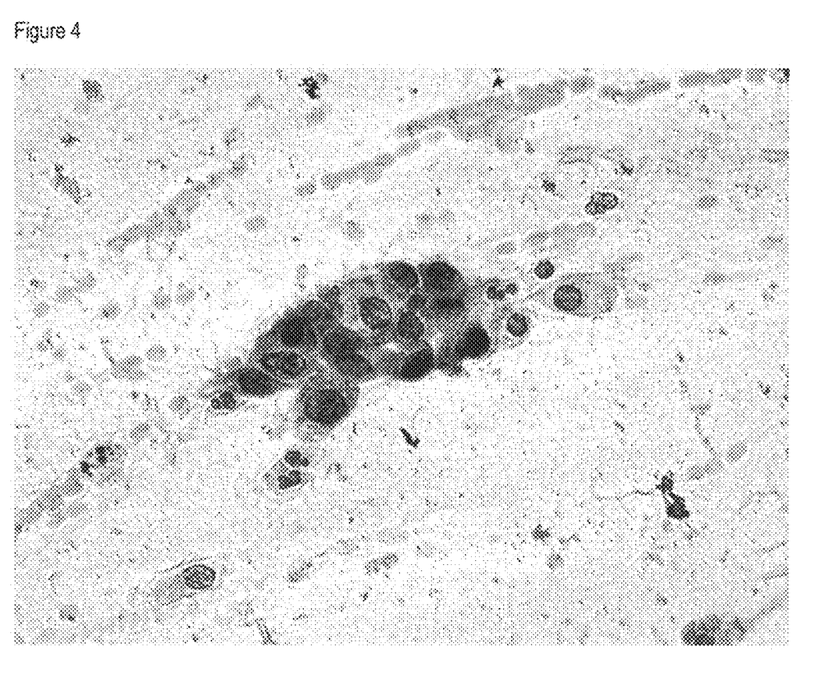
Figure 5:
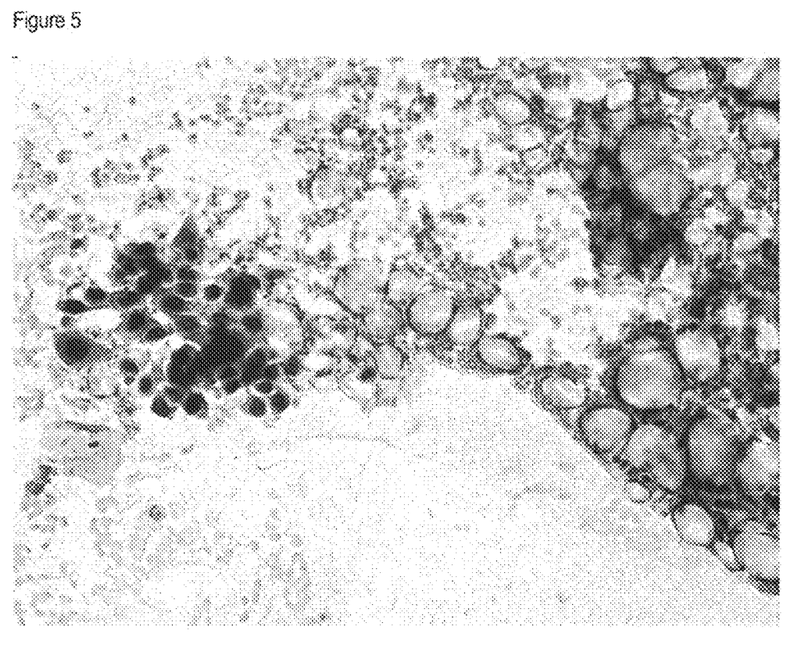
Figure 6:
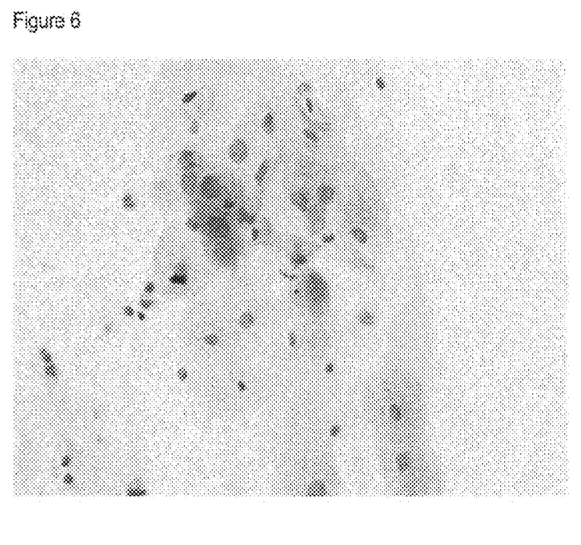
Figure 7:
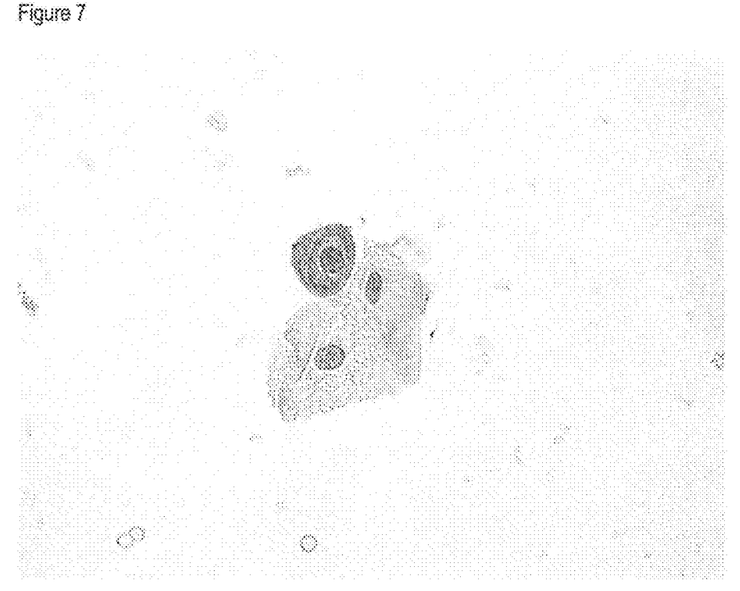
Figure 8:
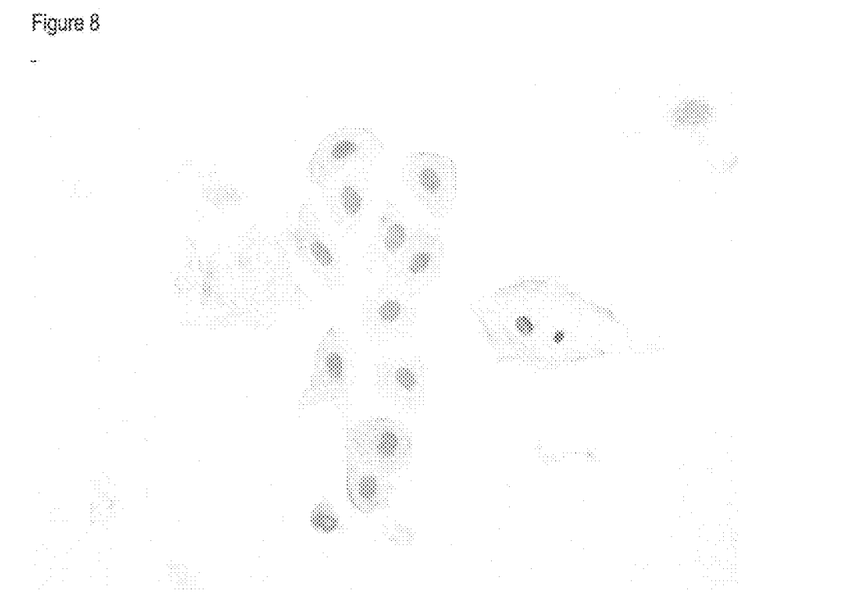
Figure 9:
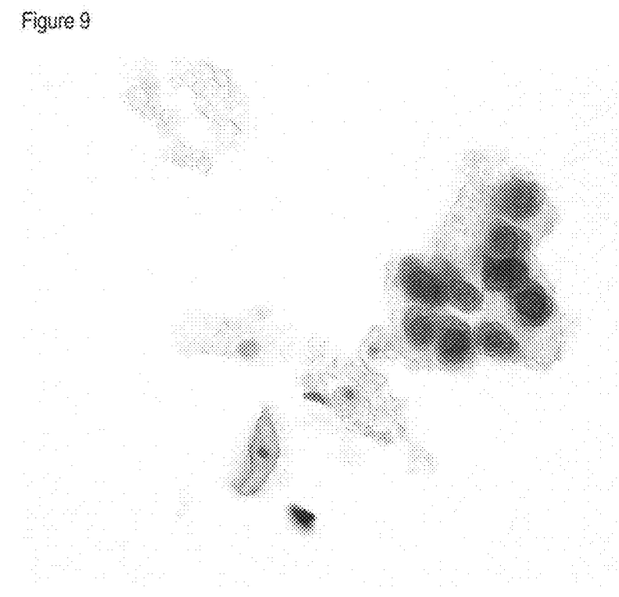
Figure 10:
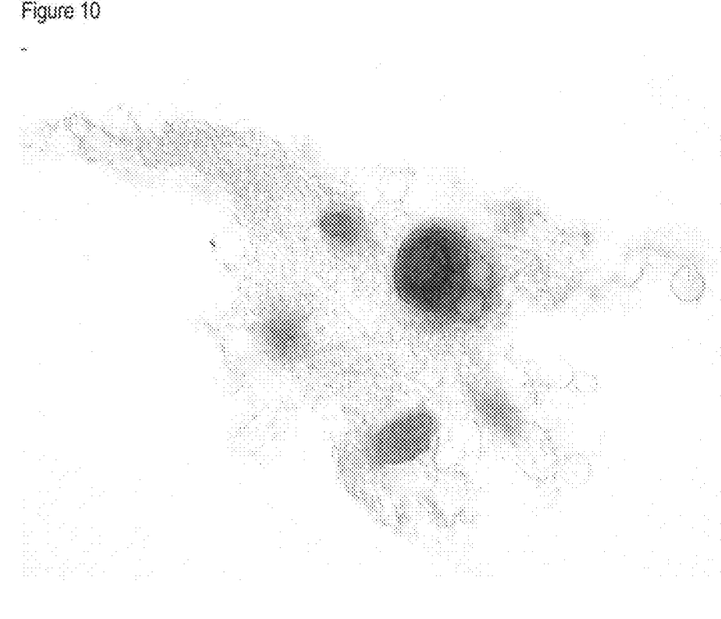
Figure 11:
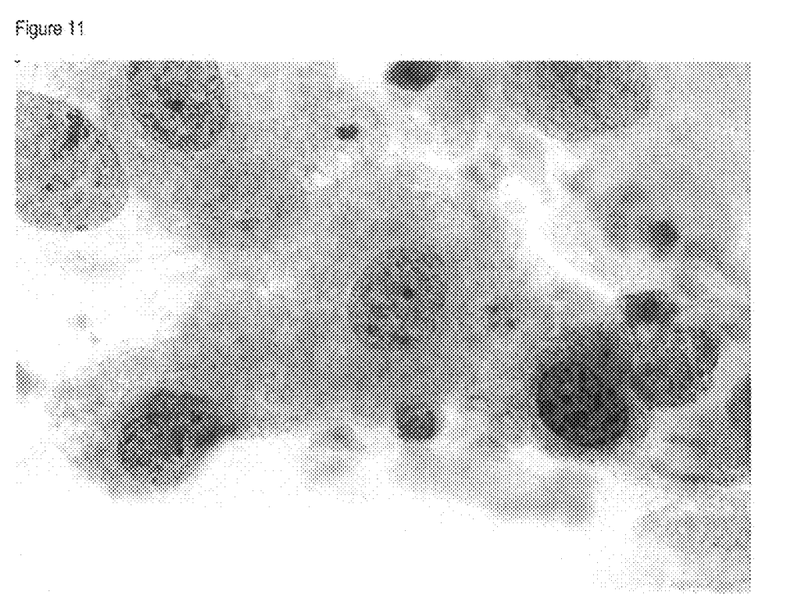

The patent or application file contains at least one drawing executed in color. Copies of the patent or patent application publication with color drawing(s) will be provided by the Office upon request and payment of the necessary fee.

The following examples are given for the purpose of illustration only and are not intended to limit the scope of the invention disclosed herein.

EXAMPLE 1

Immunochemical Detection of the Expression of HPV E2, L1 and p16$^{INK4a}$ in Samples of the Uterine Cervix Smears of the cervix uteri were immunocytochemically stained using antibodies specific for p16$^{INK4a}$ and polyclonal antibodies specific for HPV E2 protein.

For rehydration the spray-fixed smears are incubated in fresh 50% EtOH on a rocking device. The PEG film produced by the fixation procedure is removed by intensive rinsing. Following the smears are rinsed in aqua bidest. Antigen Retrieval is carried out with 10 mM citrate buffer (pH 6.0). Therefore the slides are heated in a waterbath for 40 min at 95° C., cooled down to RT for 20 minutes, transferred to washing buffer (PBS/0.1% Tween 20) and finally surrounded with a lipid-pencil.

For inactivation of endogenous peroxidase the samples are incubated with 3% $H_2O_2$ for 20 min at RT and afterwards washed in PBS/0.1% Tween 20 for 5 min. The proteinblock is carried out with horse-serum (Vectastain®-Kit) (Dilute 1:50 with PBS/0.1% Tween 20) The smears are incubate for 20 min at RT and then rinsed off carefully. Then blocking of non-specific binding of avidin—reagent is—performed as follows: Samples are incubated with avidin blocking solution (ready-to-use/Vector) for 15 min at RT and then washed carefully with pipette. For blocking of non-specific binding of biotin-reagent the smears are incubated with biotin blocking solution (ready-to-use/Vector) for 15 min at RT and then rinsed off carefully.

Then follows incubation with a p16$^{INK4a}$ specific primary antibody or polyclonal antibodies directed against HPV E2 protein or polyclonal antibodies raised against high risk (HPV16) HPV L1 protein; the samples are incubated for 60 min at RT, washed in PBS/0.1% Tween 20 for 5 min (two times) and afterwards incubated with biotinylated Secondary Antibody (horse-anti-mouse-IgG) (Vectastain®-Kit/Dilute 1:200 in PBS/0.1% Tween 20+Horse-Serum) for 30 min at RT and washed in PBS/0.1% Tween 20 for 5 min (two times) Following an incubation with AS Complex (Avidin-Biotin-HRP) (Vectastain®-Kit/Dilute 1:50 in PBS/0.1% Tween 20) is performed for 30 min at RT followed by washing steps in PBS/0.1% Tween 20 for 5 min (two times).

Signal detection is carried out with Substrate-Chromogen-Complex ($H_2O_2$/AEC) as follows: First the samples are incubate for 30 min at RT with the substrate-choromogen complex, the reaction is stopped in aqua dest. Finally a counterstain with Mayers Hematoxylin is performed and the slides are mounted with Glyceringelatine The microscopic examination of the slides reveals, that cells immunoreactive with p16$^{INK4a}$ together with cells immunoreactive with HPV E2 protein can only be found in samples, that may microscopically be identified as samples of neoplastic lesions. Cells stained by the p16$^{INK4a}$ specific reaction, that are originating from metaplasias, are not stained by the reaction specific for the HPV E2 protein. The microscopic inspection of the HPV L1 stained slides shows, that metaplastic cells are not immunoreactive with the antibodies directed against HPV L1 protein. Samples containing dysplastic cells in contrast comprise cells, that are immunoreactive with HPV L1 and those immunoreactive with p16$^{INK4a}$. So in contrast to dysplasias in metaplasias no cells may be stained using the HPV L1 specific antibody.

The results show, that the staining with reagents specific for HPV E2 or L1 allows to discriminate p16$^{INK4a}$ overexpressing metaplasias from dysplasias.

EXAMPLE 2

Detection of Cells Expressing HPV E2, HPV L1 or p16$^{INK4a}$ in Samples of the Uterine Cervix by In Situ Hybridization Smears of the uterine cervix can be semi-quantitatively analysed for the mRNA level of p16$^{INK4a}$ and HPV E2 and L2 in an in-situ staining reaction. The staining reaction is performed as follows:

For rehydration the spray-fixed smears are incubated in fresh 50% EtOH on a rocking device. The PEG film produced by the fixation procedure is removed by intensive rinsing. Following the smears are rinsed in aqua bidest. The smears are incubated with porteinase K (10 μg/ml in PBS) for 10 min at 37° C. Then the slides are transferred to washing buffer (PBS/0.1% Tween 20) and finally surrounded with a lipid-pencil.

The hybridization mixture is prepared by mixing 50 μl of ready to use hybridization buffer (DAKO A/S, Glostrup, Danmark) with about 5-10 pmol of the probes. The probes are fluorescein-labelled oligonucleotides of sequences complememtary to the respective mRNAs.

The hybridizaton mixture is heated to 95° C. and afterwards equilibrated to 37° C. After the boiling procedure the smears are each incubated with 50 μl of the hybridization mixture for 4 hours at 42° C. The samples are washed in excess volumes of the wash buffers two times in 2×SSC at 37° C. for 15 min and once in 1×SSC at 37° C. for 15 min. Then the smears are rinsed two times at room temperature in 2×SSC. Following this washing procedure the dissections are incubated for 30 min with blocking buffer (NEN, Blocking-pugger) at room temperature. Then follows 1 hour incubation with a 1:100 diluted (in Blocking buffer, see above) Anti-Fluorescein-alkaline phosphatase (DAKO A/S). The smears are then washed 2 times in 1×PBS/0.1% Triton X-100 for 10 min at room temperature, followed by one wash step with 1×PBS, 50 mM $MgCl_2$ (pH 9.2) for 10 min at room temperature. Then the staining reaction is performed with NBT/BCIP (Sigma) for 30 min to 2 hours at room temperature. The staining reaction is stopped by a short incubation with 1 mM EDTA in PBS. Finally the smears are dipped in $H_2O_{dest}$ and embedded with AquaTex (Merck). Then the stained dissections can be analysed microscopically.

Microscopic analysis reveals, that metaplasias comprise cells expressing $p16^{INK4a}$ but no cells expressing HPV L1 or E2 mRNA. In dysplastic lesions of the cervix uteri cells expressing $p16^{INK4a}$ can be found and furthermore cells expressing HPV L1 and HPV E2 mRNAs.

This result indicates, that the method according to the present invention may be used for the discrimination of metaplasias and neoplastic lesions.

EXAMPLE 3

Immunocytochemical Detection of the Expression of HPV E7, and $p16^{INK4a}$ in Samples of the Uterine Cervix ThinPrep® thinlayers of smears of the cervix uteri are immunocytochemically stained using antibodies specific for $p16^{INK4a}$ and monoclonal antibodies specific for HPV E7 protein.

For rehydration the spray-fixed smears are incubated in fresh 50% EtOH on a rocking device. The PEG film produced by the fixation procedure is removed by intensive rinsing. Following the smears are rinsed in aqua bidest. Antigen Retrieval is carried out with 10 mM citrate buffer (pH 6.0). Therefore the slides are heated in a waterbath for 40 min at 95-98° C., cooled down to RT for 20 minutes, transferred to washing buffer (Dakocytomation, S3006) and finally surrounded with a lipid-pencil.

For inactivation of endogenous peroxidase the samples are incubated with 3% $H_2O_2$ (Dakocytomation; S2023) for 5 min at RT and afterwards washed in wash buffer (Dakocytomation, S3006) for 5 min. Then follows incubation with a $p16^{INK4a}$ specific primary antibody or monoclonal antibodies directed against high risk (HPV16) E7 protein; the samples are incubated for 30 min at RT, washed in wash buffer for 5 min and afterwards incubated with the EnVision system (Dakocytomation, K4001), consisting of goat anti mouse antibodies conjugated to a dextran polymer and Peroxidase enzymes, for 30 min at RT and washed in wash buffer for 5 min (three times).

Signal detection is carried out with Substrate-Chromogen-Complex (DAB+, Dakocytomation, K3468) by incubation for 10 min at RT. The reaction is stopped in aqua dest. Finally a counterstain with Mayers Hematoxylin is performed and the slides are mounted with Faramount (DakoCytomation, S3025).

The microscopic examination of the slides reveals, that cells immunoreactive with $p16^{INK4a}$ together with cells immunoreactive with HPV E7 protein can only be found in samples, that may microscopically be identified as samples of neoplastic lesions. Cells stained by the $p16^{INK4a}$ specific reaction, that are originating from metaplasias, are not stained by the reaction specific for the HPV E7 protein.

To validate the results given herein a double staining of cytological specimens was performed using a FITC-labelled HPV E7 antibody (antibody as given above) in combination with the $p16^{INK4a}$ antibody as used above. The staining was performed as given above adapted to a double staining procedure. The necessary variations are known to those of skill in the art.

In double stained specimens no double stained metaplastic cells may be found; in contrast dysplastic cells show double staining for $p16^{INK4a}$ and HPV E7 protein.

The results show, that the staining with reagents specific for HPV E7 allows to discriminate $p16^{INK4a}$ overexpressing metaplasias from dysplasias.

What is claimed is:

1. A method for discrimination of $p16^{INK4a}$ overexpressing metaplasias from $p16^{INK4a}$ overexpressing neoplastic or pre-neoplastic lesions in a uterine cervix sample by cytological testing procedures, comprising:
    (a) measuring the presence or absence of cells overexpression of $p16^{INK4a}$ in said sample;
    (b) measuring the presence or absence of cells expressing at least one high risk HPV gene-product in said sample, wherein said high risk HPV gene-product is a polypeptide encoded by HPV E7 gene, HPV E2 gene, HPV E6 gene, HPV L1 gene, or HPV L2 gene;
    (c) assessing simultaneous presence of cells expressing the high risk HPV gene-products with cells overexpressing $p16^{INK4a}$, or assessing presence of cells overexpressing $p16^{INK4a}$ alone;
    (d) determining the simultaneous presence of cells expressing high risk HPV gene-products with cells overexpressing $p16^{INK4a}$ as indicative of neoplastic or pre-neoplastic lesion; and
    (e) determining the presence of cells overexpressing $p16^{INK4a}$ alone as indicative of metaplasias.

2. The method according to claim 1, wherein the high risk HPV gene-product is encoded by the HPV E7 gene.

3. The method according to claim 1, wherein the high risk HPV gene-product is encoded by HPV E2 or or HPV E6 gene.

4. The method according to claim 1, wherein the high risk HPV gene-product is encoded by HPV L1 or HPV L2 gene.

5. The method according to claim 1, wherein the sample is a Pap smear or a cytological preparation of the cervix uteri.

6. The method according to claim 1, wherein the measurements of the HPV gene-products and of $p16^{IMK4a}$ are performed using antibodies specific for the HPV gene-products and $p16^{INK4a}$.

7. The method according to claim 5, wherein the antibodies are detectably labelled.

8. The method according to claim 6, wherein the label is selected from the group consisting of a radioisotope, a bioluminescent compound, a chemiluminescent compound, a fluorescent compound, and an enzyme.

9. The method according to claim 1, wherein the cytological testing procedures comprise an immuno-cytochemical staining procedure.

10. The method according to claim 1, wherein the measurements of the high-risk HPV gene-product and $p16^{INK4a}$ are carried out simultaneously.

11. The method according to claim 10, wherein overexpression of $p16^{INK4a}$ and expression of at least one high risk HPV gene-product are simultaneous determined in at least one single cell.

* * * * *